US011717409B2

(12) United States Patent
DiLoreto et al.

(10) Patent No.: US 11,717,409 B2
(45) Date of Patent: *Aug. 8, 2023

(54) PENILE IMPLANT (71) Applicant: Boston Scientific Scimed, Inc., Maple Grove, MN (US)

(72) Inventors: Mark Edward DiLoreto, Chaska, MN (US); Karl Alan Jagger, Deephaven, MN (US); Thomas Skoog, Elk River, MN (US); Robert Berkenes, Buffalo, MN (US); Alex Alden Peterson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 136 days.

This patent is subject to a terminal disclaimer.

(21) Appl. No.: 17/249,886

(22) Filed: Mar. 17, 2021

(65) Prior Publication Data

US 2021/0205084 A1   Jul. 8, 2021

Related U.S. Application Data

(63) Continuation of application No. 16/052,370, filed on Aug. 1, 2018, now Pat. No. 10,980,638.
(Continued)

(51) Int. Cl.
*A61F 2/26* (2006.01)
*A61F 2/30* (2006.01)

(52) U.S. Cl.
CPC ...... *A61F 2/26* (2013.01); *A61F 2002/30476* (2013.01); *A61F 2220/0033* (2013.01);
(Continued)

(58) Field of Classification Search
CPC .................................. A61F 2/26; A61F 5/41
See application file for complete search history.

(56) References Cited

U.S. PATENT DOCUMENTS

| 3,987,789 A | 10/1976 | Timm et al. |
| 4,594,998 A | 6/1986 | Porter et al. |

(Continued)

FOREIGN PATENT DOCUMENTS

| CA | 1188052 A | 6/1985 |
| CN | 101836905 A | 9/2010 |

(Continued)

OTHER PUBLICATIONS

International Search Report and Written Opinion for International Application No. PCT/US2018/044982, dated Oct. 23, 2018, 10 pages.

(Continued)

*Primary Examiner* — Samuel G Gilbert
(74) *Attorney, Agent, or Firm* — Brake Hughes Bellermann LLP (57) ABSTRACT

According to an aspect, a penile implant includes a first member having a coupling portion and a locking portion and a second member having a coupling portion and a locking portion The coupling portion of the first member is configured to engage the coupling portion of the second member to movably couple the first member to the second member such that the first member is configured to be placed in a first position with respect to the second member and a second position with respect to the second member. The locking portion of the first member is configured to engage the locking portion of the second member help retain the first member in its second position with respect to the second member.

20 Claims, 9 Drawing Sheets

Related U.S. Application Data (60) Provisional application No. 62/541,248, filed on Aug. 4, 2017.

(52) U.S. Cl.
CPC ............... *A61F 2230/0071* (2013.01); *A61F 2250/0062* (2013.01)

(56) References Cited

U.S. PATENT DOCUMENTS

| | | |
|---|---|---|
| 4,619,251 A | 10/1986 | Helms et al. |
| 4,666,428 A | 5/1987 | Mattioli et al. |
| 5,512,033 A | 4/1996 | Westrum et al. |
| 5,553,378 A | 9/1996 | Parekh et al. |
| 8,052,593 B2 | 11/2011 | Jahns et al. |
| 10,588,747 B2 | 3/2020 | Allen et al. |
| 10,980,638 B2 | 4/2021 | Diloreto et al. |
| 2008/0103353 A1 | 5/2008 | Jahns et al. |
| 2008/0303353 A1 | 12/2008 | Wenjiang |

FOREIGN PATENT DOCUMENTS

| | | |
|---|---|---|
| CN | 102176930 A | 9/2011 |
| CN | 106255457 A | 12/2016 |

OTHER PUBLICATIONS

Office Action for AU Application No. 2018310949, dated Dec. 31, 2019, 3 pages.

Denes, "Urinary Incontinence", Asaio Transactions, vol. 34, No. 4, Oct. 1, 1988, pp. 998-999.

PENILE IMPLANT

CROSS-REFERENCE TO RELATED APPLICATION

This application is a continuation of, and claims priority to, U.S. patent application Ser. No. 16/052,370, filed on Aug. 1, 2018, entitled "PENILE IMPLANT", which claims priority to U.S. Provisional Patent Application No. 62/541,248, filed on Aug. 4, 2017, entitled "PENILE IMPLANT", the disclosures of which are incorporated by reference herein in their entirety.

TECHNICAL FIELD

This disclosure relates generally to bodily implants and more specifically to bodily implants, such as penile prostheses, that may be placed in multiple configurations.

BACKGROUND

One treatment for male erectile dysfunction is the implantation of a penile prosthesis that may be placed in a multiple configurations. For example, some existing penile prostheses may be implanted in or near the penis of the patient and may be disposed in a first configuration to place the penis in a flaccid-like state and may be disposed in a second configuration to place the penis in an erect-like state. Some existing implants include complex activation mechanisms to change the configurations of the implants and may require a large amount of effort to change or convert the implant from one configuration to another configuration.

Accordingly, it would be useful to provide a bodily implant, such as a penile prosthesis that may efficiently be moved from one configuration to another configuration.

SUMMARY

According to an aspect, a penile implant includes a first member having a coupling portion and a locking portion and a second member having a coupling portion and a locking portion The coupling portion of the first member is configured to engage the coupling portion of the second member to movably couple the first member to the second member such that the first member is configured to be placed in a first position with respect to the second member and a second position with respect to the second member. The locking portion of the first member is configured to engage the locking portion of the second member help retain the first member in its second position with respect to the second member.

In some embodiments, the coupling portion of the first member includes a cavity portion configured to receive the coupling portion of the second member. In some embodiments, the coupling portion of the first member includes a cavity portion, the coupling portion of the second member includes a protrusion portion, the cavity portion is configured to receive at least a portion of the protrusion portion. In some embodiments, the coupling portion of the first member includes a cavity having a rounded surface.

In some embodiments, the coupling portion of the second member includes a protrusion portion, the protrusion portion having a rounded surface. In some embodiments, the coupling portion of the first member includes a cavity, the locking portion of the first member being disposed within the cavity. In some embodiments, the coupling portion of the first member includes a side wall defining a cavity, the locking portion of the first member is a groove defined by the side wall.

In some embodiments, the coupling portion of the second member includes a protrusion portion, the locking portion of the second member being disposed on the protrusion portion. In some embodiments, the coupling portion of the second member includes a protrusion portion, the locking portion of the second member includes a ridge, the ridge being disposed on the protrusion portion. In some embodiments, the coupling portion of the second member includes a protrusion portion, the locking portion of the second member includes a projection disposed on the protrusion portion. In some embodiments, the coupling portion of the second member is a first coupling portion of the second member, wherein the second member includes a second coupling portion, the first coupling portion of the second member including a protrusion portion, the second coupling portion of the second member including a side wall defining a cavity.

In some embodiments, the coupling portion of the first member includes a cavity, the locking portion of the first member includes a projection, the projection being disposed within the cavity. In some embodiments, the coupling portion of the second member includes a protrusion portion, the locking portion of the second member including a groove defined on the protrusion portion.

In some embodiments, the penile implant includes a sheath defining a lumen, the lumen being configured to house the first member and the second member.

In some embodiments, the penile implant includes a first end cap coupled to the first member; a second end cap coupled to the second member; and a sheath defining a lumen, the lumen being configured to house the first member, the second member, a least a portion of the first end cap, and at least a portion of the second end cap.

Accordingly to another aspect, an apparatus includes an elongate member formed of a plurality of segment member, the elongate member configured to be placed in a first non-linear configuration and in a linear configuration, a first segment member of the plurality of segment members having a coupling portion and a locking portion, a second segment member of the plurality of segment members member having a coupling portion and a locking portion.

In some embodiments, the coupling portion of the first segment member is configured to engage the coupling portion of the second segment member to movably couple the first member to the second member. In some embodiments, the locking portion of the first segment member is configured to engage the locking portion of the second segment member help retain the elongate member in its linear configuration.

In some embodiments, the apparatus includes a sheath defining a lumen, the lumen being configured to house the plurality of segment members.

According to another aspect, a penile implant includes an elongate member formed of a plurality of segment member, a first end member, and a second end member, the elongate member configured to be placed in a first non-linear configuration and in a linear configuration; and a sheath defining a lumen, the lumen being configured to house the plurality of segment members, at least a portion of the first end member, and at least a portion of the second end member, a first segment member of the plurality of segment members having a coupling portion and a locking portion, a second segment member of the plurality of segment members member having a coupling portion and a locking portion.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices or implants such as penile prostheses or other bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The terms proximal and distal described in relation to various devices, apparatuses, and components as discussed in the subsequent text of the present disclosure are referred with a point of reference. The point of reference, as used in this description, is a perspective of a person who implants the device such as the penile prosthesis. The person may be a surgeon, a physician, a nurse, a doctor, a technician, and the like who may perform the implantation procedure. The term proximal refers to an area or portion that is closer or closest to the person during the implantation procedure. The term distal refers to an area or portion that is farther or farthest from the person.

The embodiments discussed herein may improve the performance of a penile prosthesis. For example, the penile prosthesis may have improved usability. Specifically, the penile prosthesis may require a small amount of effort to convert the implant from a first configuration to a second configuration. Additionally, the penile prosthesis may require less effort to implant the device into the body of a patient.

Figure 1:
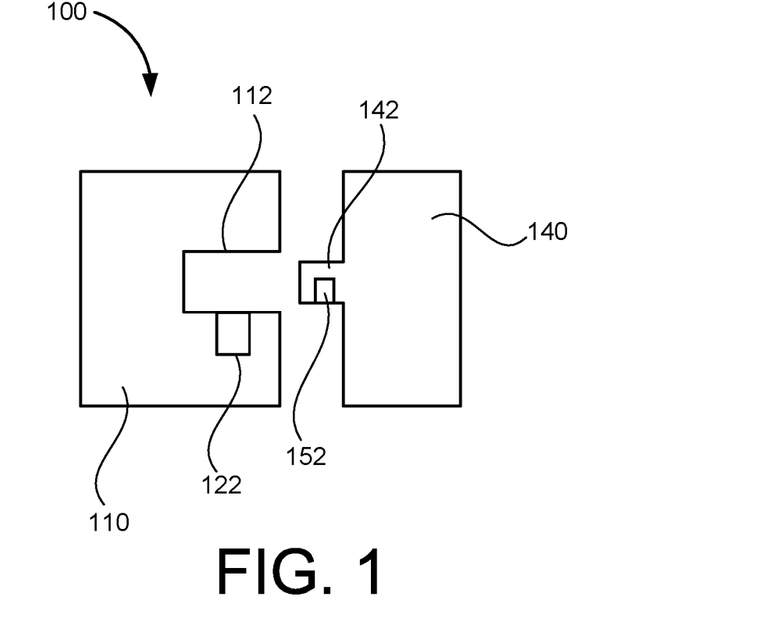
FIG. 1 schematically illustrates a penile prosthesis according to an embodiment.

FIG. 1 schematically illustrates a prosthesis or an implant 100 according to an aspect. The implant includes a first member 110 and a second member 140. The implant 100 may be disposed or placed within a body of a patient or user. For example, in some embodiment, the implant 100 may be a penile implant and the implant 100 may be placed within a penis of a patient. Specifically, in some embodiments, the implant 100 may be implanted within the corpus cavernosae of the patient. In other embodiments, the implant may be placed in other locations within the body of the patient.

In some embodiments, more than one implant 100 may be placed within the body of the patient. For example, in some embodiments, two implants 100 may be placed within the body of the patient. Specifically, in some embodiments, two implants 100 may be placed within a penis of the patient. The implants may be placed within the penis of the patient in substantially parallel or a side-by-side arraignment. In other embodiments, only one implant 100 is disposed or implanted within the body of the patient.

The implant 100 may be placed in a first configuration and a second configuration different than the first configuration. For example, in some embodiments, the implant 100 may be able to be placed in a straight or linear configuration and in a curved or non-linear configuration. Accordingly, in some embodiments, the implant 100 may be placed within a penis of the patient and the patient may selectively place the implant in (1) a straight or linear configuration to achieve or simulate an erect penis or (2) a curved or non-linear configuration to achieve or simulate a flaccid penis.

The first member 110 includes a coupling portion 112 and a locking portion 122. The second member 140 includes a coupling portion 142 and a locking portion 152.

The coupling portion 112 of the first member 110 is configured to engage or interact with the coupling portion 142 of the second member 140 to couple the first member 110 to the second member 140. For example, the first member 110 may be coupled to the second member 140 such that the first member 110 may move with respect to the second member 140 (and the second member 140 may move with respect to the first member 110). In some embodiments, the members may move with respect to each other such that the members may be placed in a straight or linear configuration and a curved or non-linear configuration.

In some embodiments, the coupling portion 112 of the first member 110 is configured to frictionally engage the coupling portion 142 of the second member 140 to frictionally couple the first member 110 to the second member 120.

For example, in some embodiments, the coupling portion 112 of the first member 110 is a cavity or opening and the coupling portion 142 of the second member 140 is a protrusion. The cavity or opening is configured to receive the protrusion to couple the first member 110 to the second member 140. In other embodiments, other types of coupling or coupling portions may be used to couple the first member 110 to the second member 140.

The locking portion 122 of the first member 110 is configured to engage or interact with the locking portion 152 of the second member 140. For example, the locking portions 122 and 152 may engage or contact each other when the member 110 and 140 are disposed in a specific configuration to help retain the members 110 and 140 in that configuration. In some embodiments, the locking portions 122 and 152 are configured to help retain the members 110 and 140 in their straight or linear configuration.

In some embodiments, the locking portion 122 of the first member 110 is a groove or opening and the locking portion 152 of the second member 140 is a ridge or projection. The groove or opening is configured to receive the ridge or projection to lock or help retain the members 110 and 140 in a specific configuration or orientation with respect to each other. In other embodiments, the locking portions may have different configurations to lock the members in place with respect to each other.

In some embodiments, a plurality of members may be coupled together to form a bodily implant such as a penile implant. More or less of the members may be serially coupled together to form different sized implants. For example, in one embodiment, 15 members may be coupled together to form an implant of a first length or size and in another embodiment, 20 members may be coupled together to form an implant of a larger size.

In some embodiments, the implant may include end members or end caps as well as a sheath such as an outer sheath. In some embodiments, the sheath may define a lumen that is configured to house or retain the members of the implant.

Figures 2, 3:
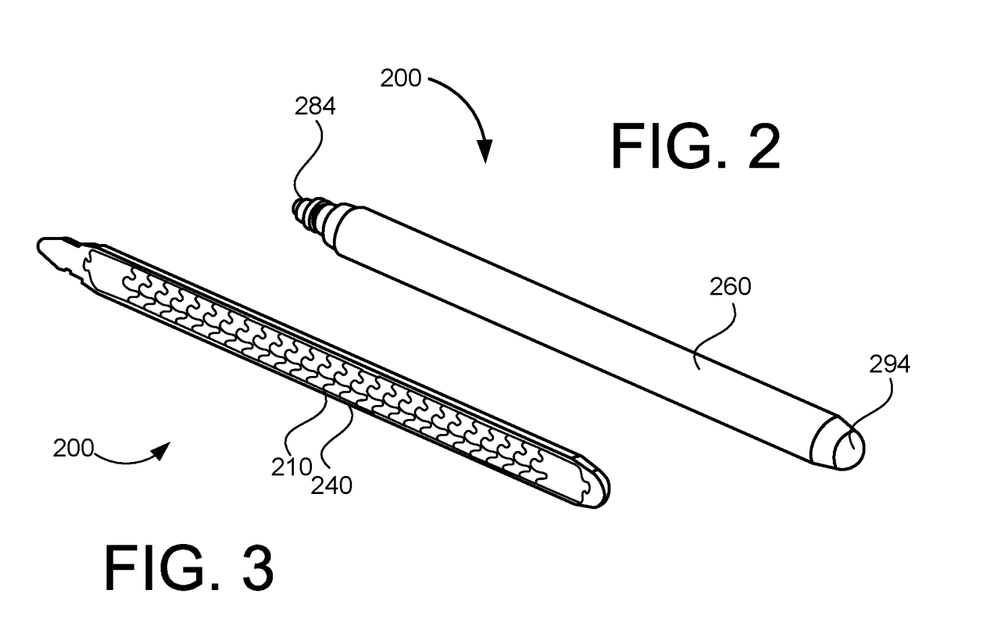
FIG. 2 is a perspective view of a penile prosthesis according to an embodiment.
FIG. 3 is a cross-sectional view of the penile prosthesis of FIG. 2.
Figures 4, 5:
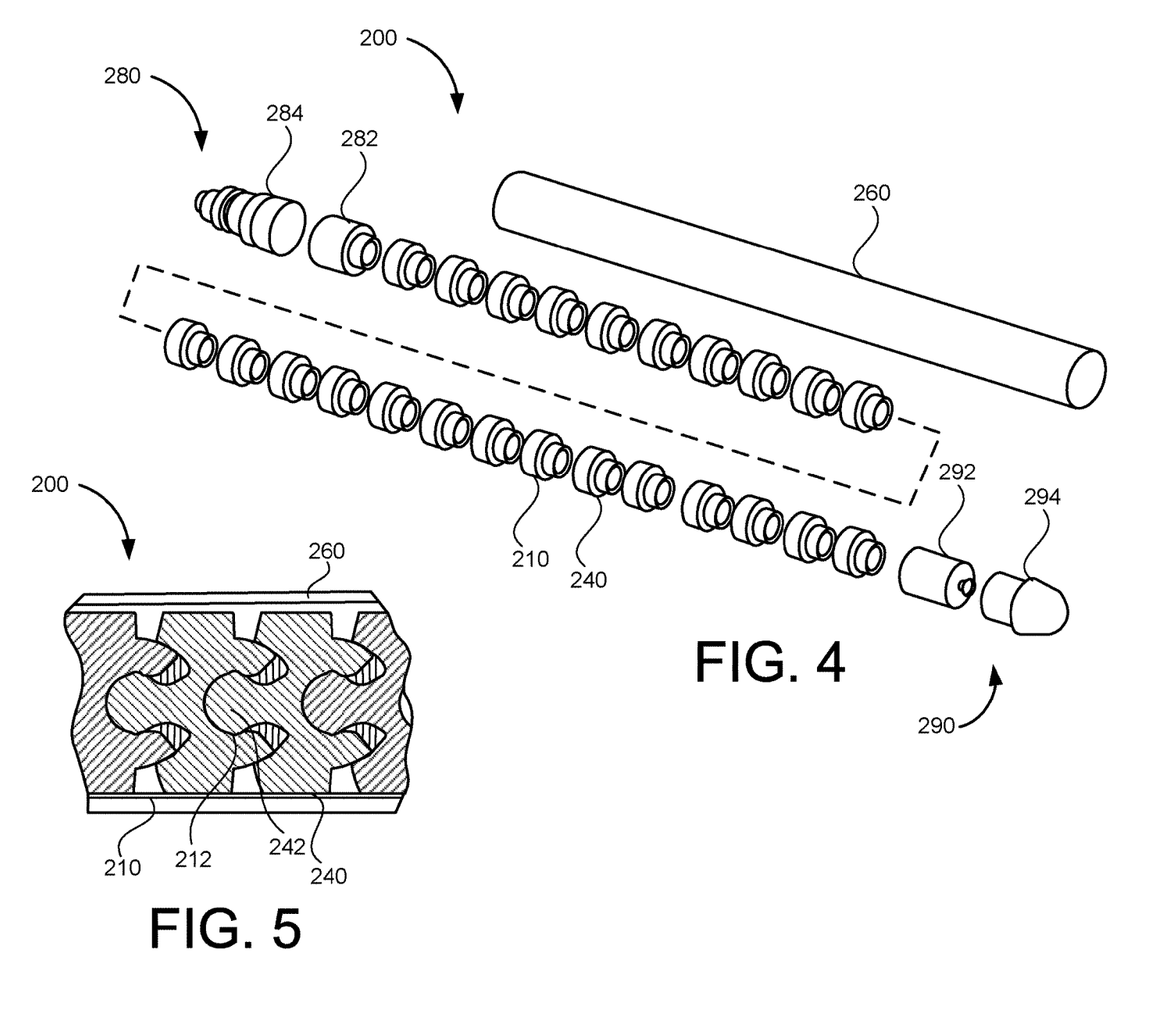
FIG. 4 is an exploded view of the penile prosthesis of FIG. 2.
FIGS. 5, 6, and 7 are cross-sectional views of portions of the penile prosthesis of FIG. 2.
Figure 6:
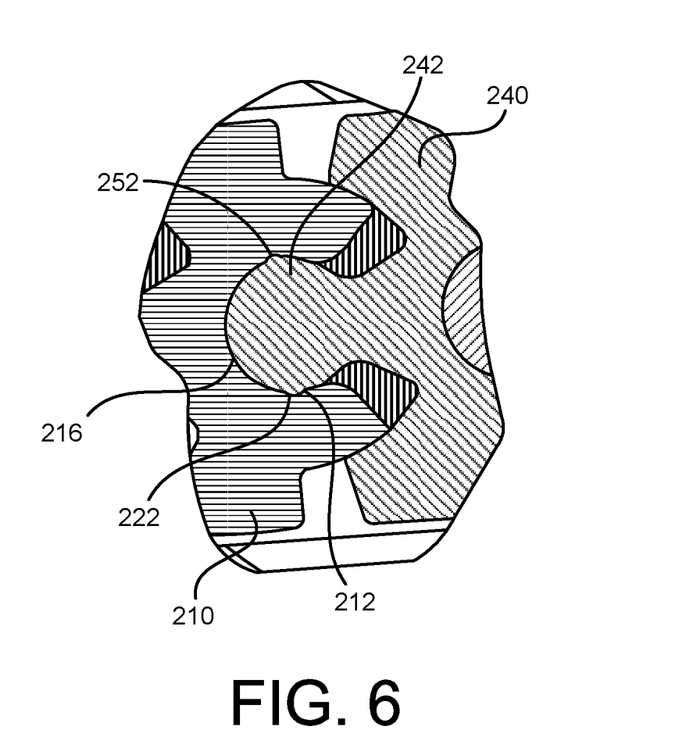
Figure 7:
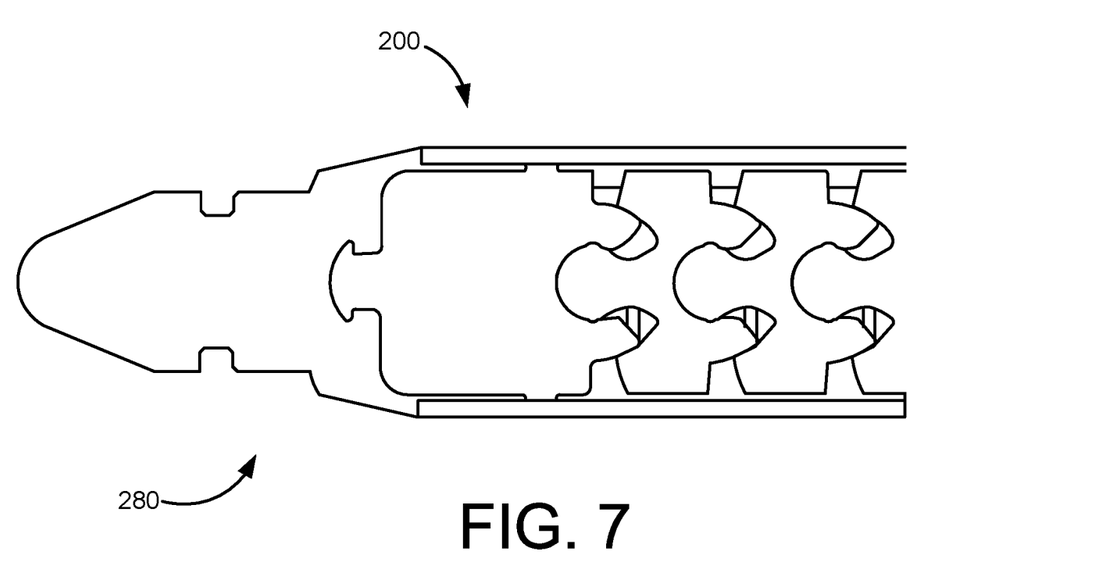
Figure 8:
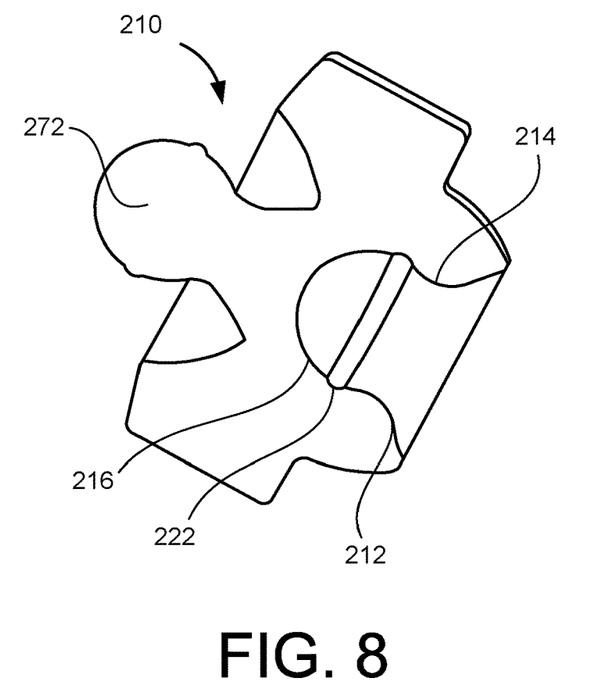
FIG. 8 is a cross-sectional view of a member of the penile prosthesis of FIG. 2.
Figure 9:
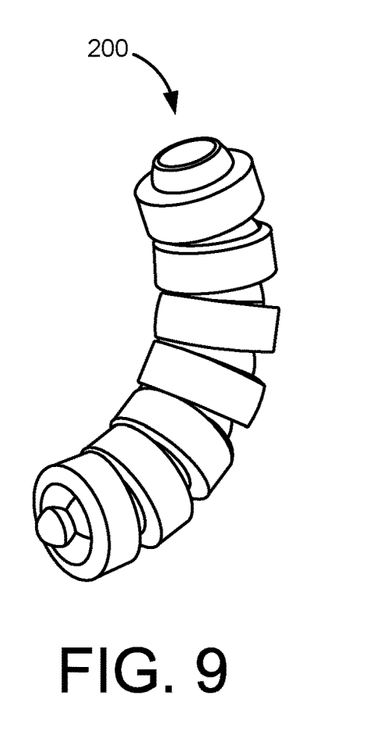
FIG. 9 is a perspective view of a portion of the penile prosthesis of FIG. 2 in a non-linear configuration.
Figure 10:
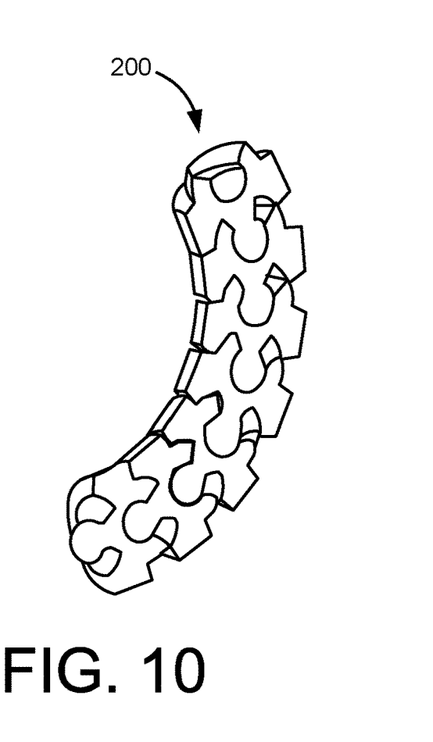
FIG. 10 is a cross-sectional view of the portion of the penile prosthesis of FIG. 9 in a non-linear configuration.
Figure 11:
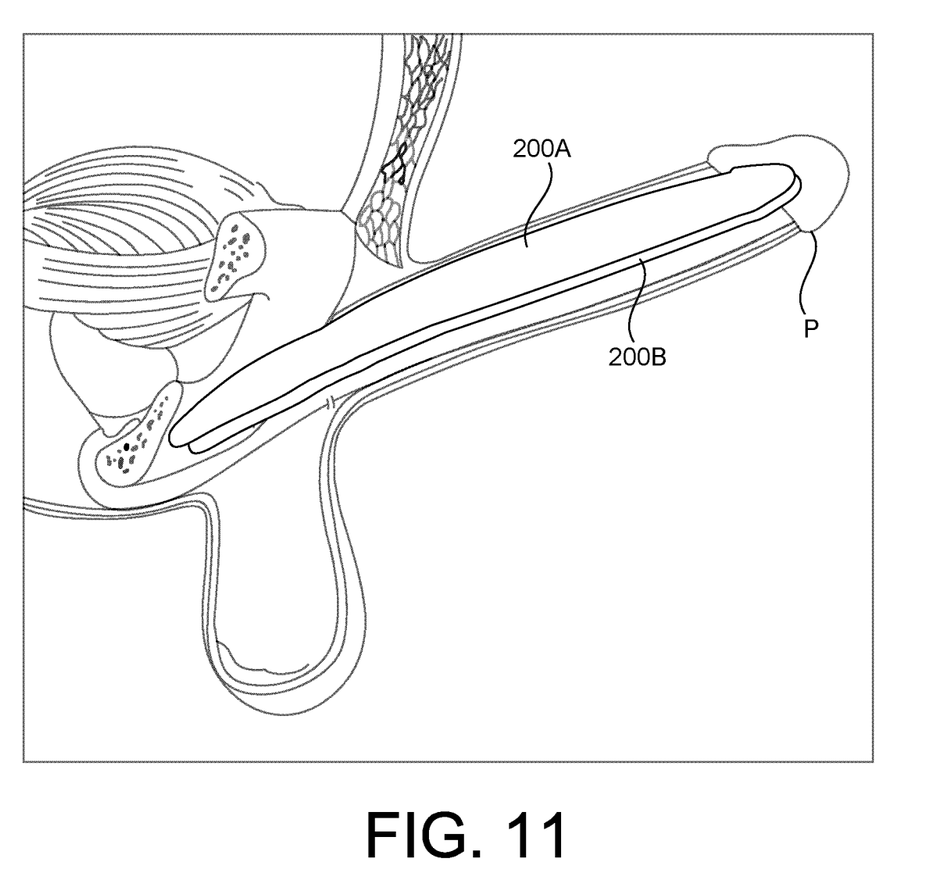
FIG. 11 is a schematic illustration of the penile prosthesis of FIG. 2 disposed within a body of a patient.

FIGS. 2-11 illustrate an implant or penile prosthesis 200 according to an aspect. FIG. 2 is a perspective view of a penile prosthesis according to an embodiment. FIG. 3 is a cross-sectional view of the penile prosthesis 200. FIG. 4 is an exploded view of the penile prosthesis 200. FIGS. 5, 6, and 7 are cross-sectional views of portions of the penile prosthesis 200. FIG. 8 is a cross-sectional view of a member of the penile prosthesis 200. FIG. 9 is a perspective view of a portion of the penile prosthesis 200 in a non-linear configuration. FIG. 10 is a cross-sectional view of the portion of the penile prosthesis 200 in a non-linear configuration. FIG. 11 is a schematic illustration of the penile prosthesis 200 disposed within a body of a patient.

The implant 200 includes a plurality of members. Each of the members is structurally and functionally similar. Accordingly, portions of a first member 210 and a second member 240 will be described in detail below.

The implant 200 may be disposed or placed within a body of a patient or user. For example, in some embodiment, the implant 200 may be a penile implant and the implant 200 may be placed within a penis of a patient. Specifically, in some embodiments, the implant 200 may be implanted within the corpus cavernosae of the patient. In other embodiments, the implant may be placed in other locations within the body of the patient.

In some embodiments, more than one implant 200 may be placed within the body of the patient. For example, in some embodiments, two implants 200 may be placed within the body of the patient. Specifically, in some embodiments, two implants 200 may be placed within a penis of the patient. The implants may be placed within the penis of the patient in substantially parallel or a side-by-side arraignment. In other embodiments, only one implant 200 is disposed or implanted within the body of the patient.

The implant 200 may be placed in a first configuration and a second configuration different than the first configuration. For example, in some embodiments, the implant 200 may be able to be placed in a straight or linear configuration and in a curved or non-linear configuration. Accordingly, in some embodiments, the implant 200 may be placed within a penis of the patient and the patient may selectively place the implant in (1) a straight or linear configuration to achieve or simulate an erect penis or (2) a curved or non-linear configuration to achieve or simulate a flaccid penis.

The first member 210 includes a coupling portion 212 and a locking portion 222. The second member 240 includes a coupling portion 242 and a locking portion 252.

The coupling portion 212 of the first member 210 is configured to engage or interact with the coupling portion 242 of the second member 240 to couple the first member 210 to the second member 240. The first member 210 is coupled to the second member 240 such that the first member 210 may move with respect to the second member 240 (and the second member 240 may move with respect to the first member 210). The members 210 and 240 may move with respect to each other such that the members may be placed in a straight or linear configuration and a curved or non-linear configuration.

In the illustrated embodiment, the coupling portion 212 of the first member 210 is a cavity or opening 214. Specifically, the first member 210 includes a sidewall 216 that defines the cavity or opening 214. In the illustrated embodiment, the sidewall 216 defines a spherical-like or hemispherical-like cavity or opening. In other embodiments, the cavity or opening has a different shape.

In the illustrated embodiment, the coupling portion 242 of the second member 240 includes a protrusion or protrusion portion 244. The protrusion or protrusion portion 244 is spherical-like in shape. In other embodiments, the protrusion or protrusion portion has a different shape.

The cavity or opening 214 is configured to receive the protrusion or protrusion portion 244 to couple the first member 210 to the second member 240. Similar to a ball and socket type joint, the coupling between the cavity 214 and the protrusion 244 allows the members 210 and 240 to move with respect to each other. As best illustrated in FIG. 6, the coupling between the cavity 214 and the protrusion 244 allows for movement to plus and minus seventeen degrees from the centerline. In other embodiments, the coupling may allow for more movement. In yet other embodiments, the coupling may allow for less movement.

The locking portion 222 of the first member 210 is configured to engage or interact with the locking portion 252 of the second member 240. For example, the locking portions 222 and 252 may engage or contact each other when the members 210 and 240 are disposed in a specific configuration to help retain the members 210 and 240 in that configuration. In the illustrated embodiment, the locking portions 222 and 252 are configured to help retain the members 210 and 240 in their straight or linear configuration.

In the illustrated embodiment, the locking portion 222 of the first member 210 is a groove or opening 224. The groove or opening 224 is located or disposed within the cavity 214. Specifically, the groove or opening 224 is defined by the sidewall 216 that forms or defines the cavity 214. In the illustrated embodiment, the groove or opening 224 extends around the cavity or opening 214 to form a complete circle. In other embodiments, the groove or opening 224 has a different size or shape.

In the illustrated embodiment, the locking portion 252 of the second member 240 is a ridge or projection 254. The ridge or projection 254 is located on the protrusion portion 244 of the second member 240. Specifically, the ridge or projection extends about the surface of the protrusion portion 244 to form a complete circle. In other embodiments, the ridge or projection has a different shape or size.

The groove or opening 224 is configured to receive the ridge or projection 254 to lock or help retain the members 210 and 240 in a specific configuration or orientation with respect to each other. In the illustrated embodiment, the groove or opening 224 is configured to receive the ridge or projection 254 when the members 210 and 240 are placed in their straight or linear configuration to lock or help retain the members 210 and 240 in such a configuration. In other embodiments, the locking portions may have different configurations to lock the members in place with respect to each other.

FIG. 8 is a cross-sectional view of first member 210. As discussed above, the first member 210 includes a coupling portion 212 (cavity or opening). The first member 210 also includes a second coupling portion 272 (protrusion or protrusion portion). Accordingly, the implant 200 includes many members that may be serially coupled together to form the bodily implant 200 such as a penile implant. More or less of the members may be serially coupled together to form different sized implants. For example, in one embodiment, 15 members may be coupled together to form an implant of a first length or size and in another embodiment, 20 members may be coupled together to form an implant of a larger size.

In the illustrated embodiment, the implant 200 includes a rear end assembly 280 and a front end assembly 290. The rear end assembly 280 includes a rear end member 282 and a rear end cap 284. The rear end member 282 includes a first end portion coupled to the rear most member and a second end portion coupled to the rear end cap 284. The front end assembly 290 includes a front end member 292 and a front end cap 294. The front end member includes a first end portion coupled to the front most member and a second end portion coupled to the front end cap 294.

The implant 200 also includes a sheath 260. The sheath 260 defines a lumen 262. In the illustrated embodiment, the sheath 260 is configured to house or surround most or all of the members. Specifically, the lumen 262 is configured to house the members. In other words, the members, including the first member 210 and the second member 240, are disposed within the lumen 262 of the sheath 260. In the illustrated embodiment, the sheath 260 is coupled to and extends from the rear end cap 284 to the front end cap 294. In some embodiments, the sheath 260 may be formed of a bioabsorbable material.

As illustrated in FIG. 11, the implant may be placed or disposed within a penis P of a patient or user. In the illustrated embodiment, a first implant 200A and a second implant 200B are disposed or placed within the penis of the patient. The implants are placed in a parallel or side-by-side relationship (with the urethra of the patient extending between the implants). In some embodiments, only one implant is disposed within the patient. Additionally, in some embodiments, the implant is placed or disposed in another portion of the body of the patient.

In use, a user or patient may straighten their penis to place the implant 200 in its first, straight, or linear configuration. For example, a user may grasp and lift an end of their penis to straighten their penis and place the implant 200 in its first, straight, or linear configuration. The lifting and end portion or straightening of the implant 200 will cause locking members of the members to engage with the locking members of the adjacent members. In this configuration, the implant 200 is retained in its first, straight, or linear configuration.

A user or patient may push their penis down or into a non-linear position. This movement will overcome the locking force of the locking portions and will release the implant 200 from its first, straight, or linear configuration. Specifically, the implant 200 will be returned to its second, curved or non-linear configuration.

Figure 12:
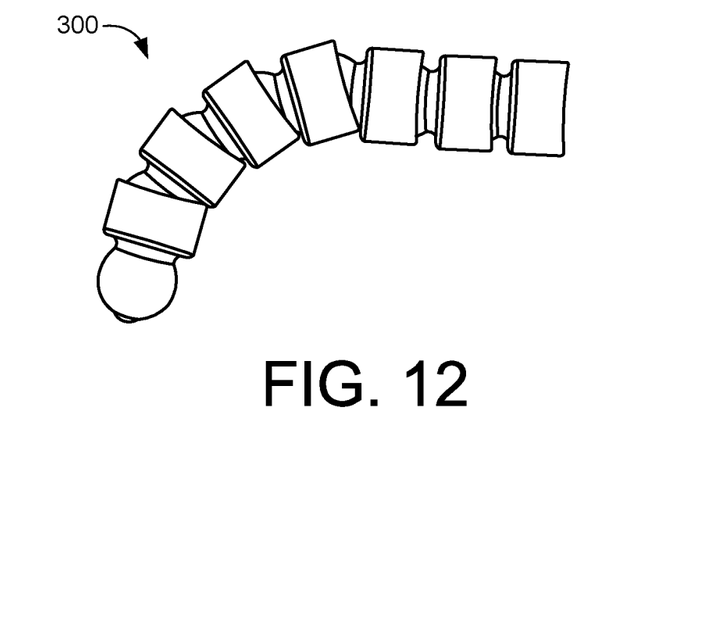
FIG. 12 is a side view of a penile prosthesis according to an embodiment.
Figure 13:
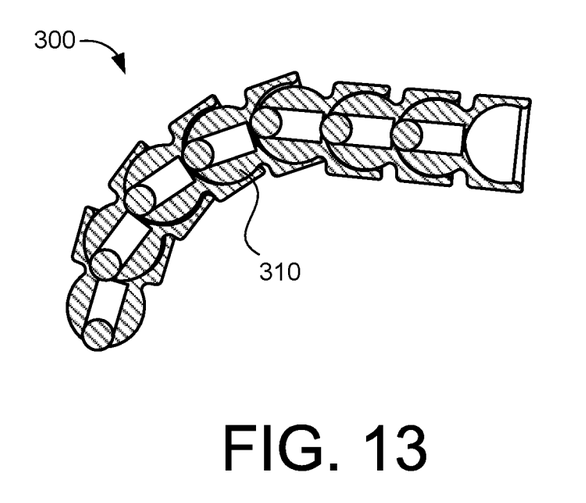
FIG. 13 is a cross-sectional view of the penile prosthesis of FIG. 12.
Figure 14:
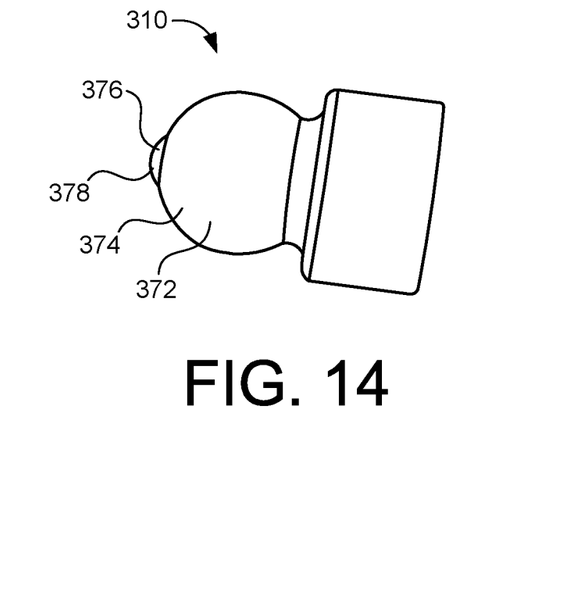
FIG. 14 is a side view of a member of the penile prosthesis of FIG. 12.
Figure 15:
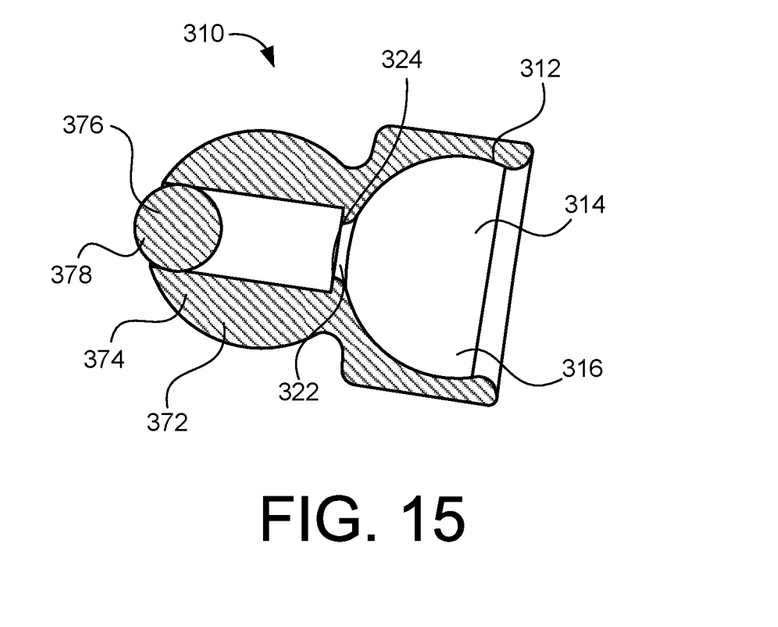
FIG. 15 is a cross-sectional view of the member of FIG. 14.

FIGS. 12-15 illustrate an implant or penile prosthesis 300 according to an aspect. FIG. 12 is a side view of the penile prosthesis 300 according to an embodiment. FIG. 13 is a cross-sectional view of the penile prosthesis 300. FIG. 14 is a side view of a member 310 of the penile prosthesis 300. FIG. 15 is a cross-sectional view of the member 310.

The implant 300 includes a plurality of members. Each of the members is structurally and functionally similar. Accordingly, only member 310 will be described in detail below.

The implant 300 may be disposed or placed within a body of a patient or user. For example, in some embodiment, the implant 300 may be a penile implant and the implant 300 may be placed within a penis of a patient. Specifically, in some embodiments, the implant 300 may be implanted within the corpus cavernosae of the patient. In other embodiments, the implant may be placed in other locations within the body of the patient.

In some embodiments, more than one implant 300 may be placed within the body of the patient. For example, in some embodiments, two implants 300 may be placed within the body of the patient. Specifically, in some embodiments, two implants 300 may be placed within a penis of the patient. The implants may be placed within the penis of the patient in substantially parallel or a side-by-side arraignment. In other embodiments, only one implant 300 is disposed or implanted within the body of the patient.

The implant 300 may be placed in a first configuration and a second configuration different than the first configuration. For example, in some embodiments, the implant 300 may be able to be placed in a straight or linear configuration and in a curved or non-linear configuration. Accordingly, in some embodiments, the implant 300 may be placed within a penis of the patient and the patient may selectively place the implant in (1) a straight or linear configuration to achieve or simulate an erect penis or (2) a curved or non-linear configuration to achieve or simulate a flaccid penis.

The member 310 includes a first coupling portion 312 and a first locking portion 322. The member 310 also includes a second coupling portion 372 and a second locking portion 374.

The first coupling portion 312 of the member 310 is configured to engage or interact with a coupling portion of another member to couple the member 310 to the other member. The member 310 is coupled to the other member such that the member 310 may move with respect to the other member (and the other member may move with respect to the member 310). The second coupling portion 372 of the member 310 is configured to engage or interact with a coupling portion of yet another member to couple the member 310 to the yet other member.

The members may move with respect to each other such that the members may be placed in a straight or linear configuration and a curved or non-linear configuration.

In the illustrated embodiment, the first coupling portion 312 of the member 310 is a cavity or opening 314. Specifically, the member 310 includes a sidewall 216 that defines the cavity or opening 314. In the illustrated embodiment, the sidewall 316 defines a spherical-like or hemispherical-like cavity or opening. In other embodiments, the cavity or opening has a different shape.

The second coupling portion 372 of the member 310 includes a protrusion or protrusion portion 374. The protrusion or protrusion portion 374 is spherical-like in shape. In other embodiments, the protrusion or protrusion portion has a different shape.

The cavity or opening 314 is configured to receive the protrusion or protrusion portion of another member to couple the member 310 to the other member.

A first locking portion 322 of the member 310 is configured to engage or interact with a locking portion of another member to help retain the members in a specific configuration. In the illustrated embodiment, the locking portions are configured to help retain the members in their straight or linear configuration.

In the illustrated embodiment, the first locking portion 322 of the member 310 is an opening or a detent 324. The opening or detent 324 is located or disposed within the cavity 314.

In the illustrated embodiment, a second locking portion 376 of the member 310 is a projection 378. The projection 378 is located on the protrusion portion 372 of the member 310. The opening or detent 324 is configured to receive the projection of an adjacent member to lock or help retain the members in a specific configuration or orientation with respect to each other.

Figure 16:
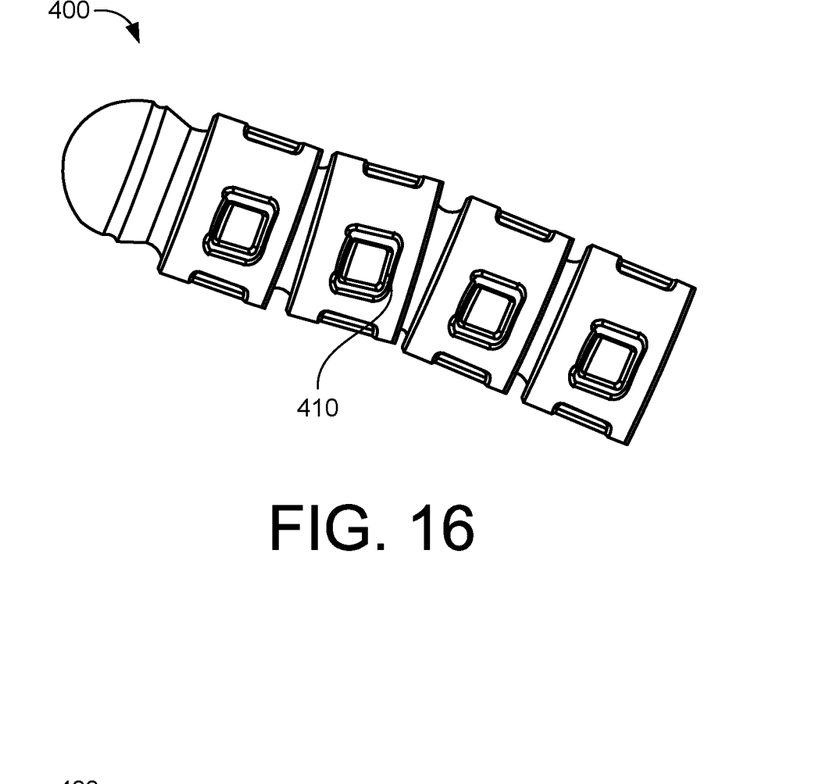
FIG. 16 is a side view of a penile prosthesis according to an embodiment.
Figure 17:
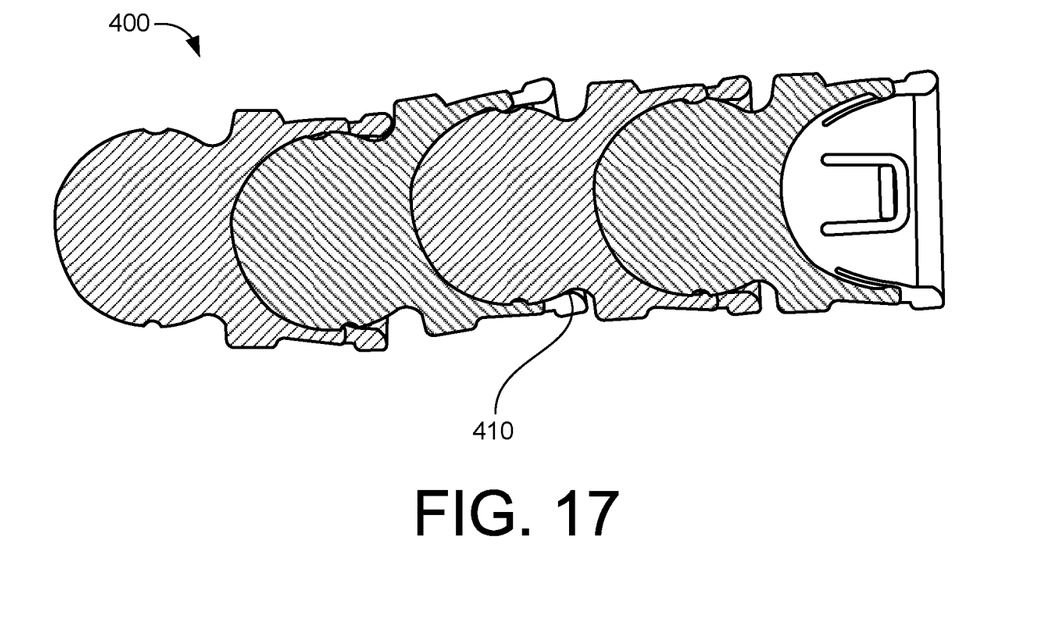
FIG. 17 is a cross-sectional view of the penile prosthesis of FIG. 16.
Figure 18:
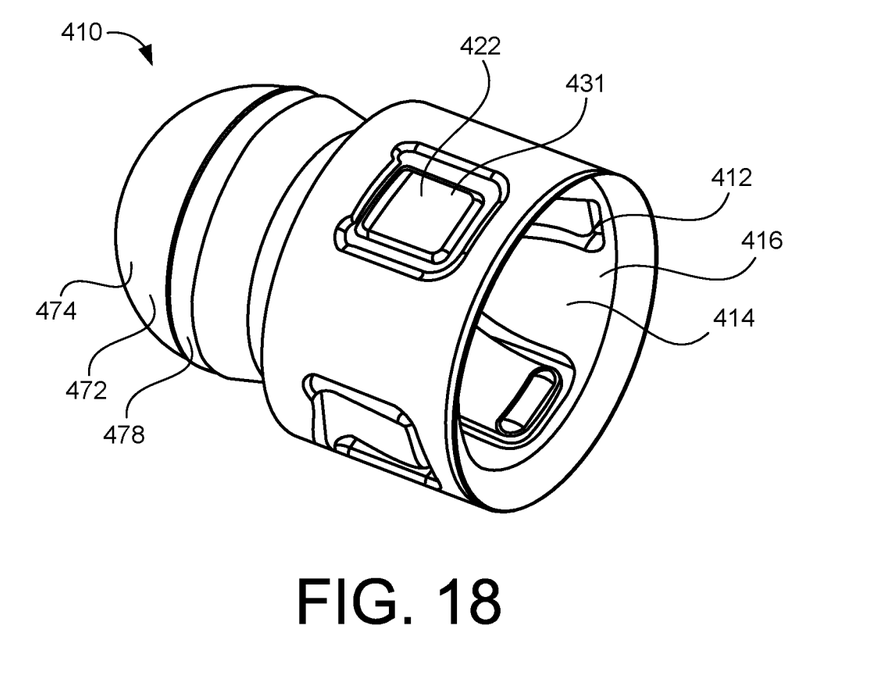
FIG. 18 is a perspective view of a member of the penile prosthesis of FIG. 16.
Figure 19:
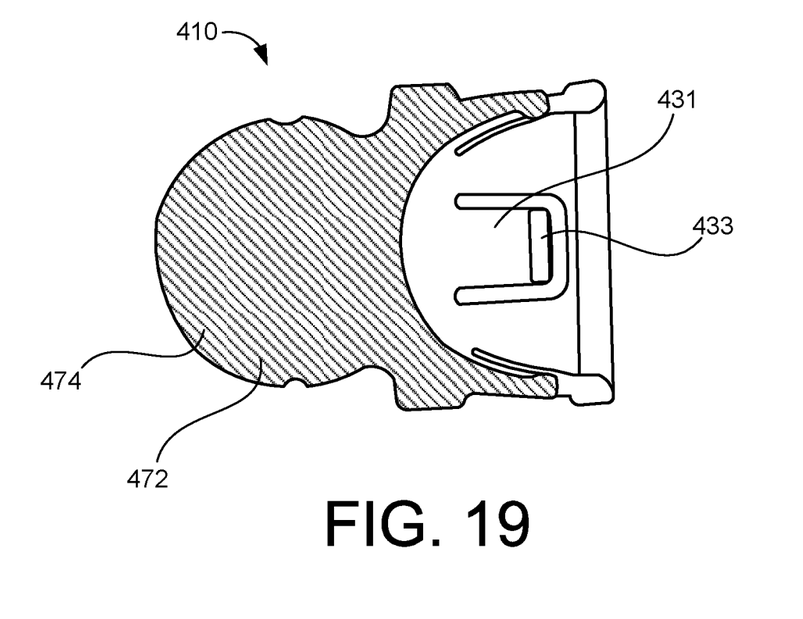
FIG. 19 is a cross-sectional view of the member of FIG. 18.

FIGS. 16-19 illustrate an implant or penile prosthesis 400 according to an aspect. FIG. 16 is a side view of the penile prosthesis 400. FIG. 17 is a cross-sectional view of the penile prosthesis 400. FIG. 18 is a perspective view of a member 410 of the penile prosthesis 400. FIG. 19 is a cross-sectional view of the member 410.

The implant 400 includes a plurality of members. Each of the members is structurally and functionally similar. Accordingly, only member 410 will be described in detail below.

The implant 400 may be disposed or placed within a body of a patient or user. For example, in some embodiment, the implant 400 may be a penile implant and the implant 400 may be placed within a penis of a patient. Specifically, in some embodiments, the implant 400 may be implanted within the corpus cavernosae of the patient. In other embodiments, the implant may be placed in other locations within the body of the patient.

In some embodiments, more than one implant 400 may be placed within the body of the patient. For example, in some embodiments, two implants 400 may be placed within the body of the patient. Specifically, in some embodiments, two implants 300 may be placed within a penis of the patient. The implants may be placed within the penis of the patient in substantially parallel or a side-by-side arraignment. In other embodiments, only one implant 400 is disposed or implanted within the body of the patient.

The implant 400 may be placed in a first configuration and a second configuration different than the first configuration. For example, in some embodiments, the implant 400 may be able to be placed in a straight or linear configuration and in a curved or non-linear configuration. Accordingly, in some embodiments, the implant 400 may be placed within a penis of the patient and the patient may selectively place the implant in (1) a straight or linear configuration to achieve or simulate an erect penis or (2) a curved or non-linear configuration to achieve or simulate a flaccid penis.

The member 410 includes a first coupling portion 412 and a first locking portion 422. The member 410 also includes a second coupling portion 472 and a second locking portion 474.

The first coupling portion 412 of the member 410 is configured to engage or interact with a coupling portion of another member to couple the member 410 to the other member. The member 410 is coupled to the other member such that the member 410 may move with respect to the other member (and the other member may move with respect to the member 410). The second coupling portion 472 of the member 410 is configured to engage or interact with a coupling portion of yet another member to couple the member 410 to the yet other member.

The members may move with respect to each other such that the members may be placed in a straight or linear configuration and a curved or non-linear configuration.

In the illustrated embodiment, the first coupling portion 412 of the member 410 is a cavity or opening 414. Specifically, the member 410 includes a sidewall 416 that defines the cavity or opening 414.

The second coupling portion 472 of the member 410 includes a protrusion or protrusion portion 474. The protrusion or protrusion portion 474 is spherical-like in shape. In other embodiments, the protrusion or protrusion portion has a different shape.

The cavity or opening 414 is configured to receive the protrusion or protrusion portion of another member to couple the member 410 to the other member.

A first locking portion 422 of the member 410 is configured to engage or interact with a locking portion of another member to help retain the members in a specific configuration. In the illustrated embodiment, the locking portions are configured to help retain the members in their straight or linear configuration.

In the illustrated embodiment, the first locking portion 422 of the member 410 includes a tab member 431 and a projection 433. The tab member 431 is configured to flex and the projection 433 extends into the cavity or opening 414. In the illustrated embodiment, the member 410 includes more than one tab and projection. In other embodiments, one or more than one tab and projection are included.

In the illustrated embodiment, a second locking portion 476 of the member 410 is a groove or opening 478. The groove or opening 478 is located on the protrusion portion 472 of the member 410. The groove or opening 478 is configured to receive the projection of an adjacent member to lock or help retain the members in a specific configuration or orientation with respect to each other.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A penile implant, comprising:
 a first member having a coupling portion and a locking portion, the locking portion including a first flexible tab member and a second flexible tab member; and
 a second member having a coupling portion and a locking portion, the coupling portion of the first member configured to engage the coupling portion of the second member to movably couple the first member to the second member such that the first member is configured to be placed in a first position with respect to the second member and a second position with respect to the second member, the locking portion of the first member being configured to engage the locking portion of the second member help retain the first member in its second position with respect to the second member.

2. The penile implant of claim 1, wherein the coupling portion of the first member includes a cavity portion configured to receive the coupling portion of the second member.

3. The penile implant of claim 1, wherein the coupling portion of the first member includes a cavity portion, the coupling portion of the second member includes a protrusion portion, the cavity portion is configured to receive at least a portion of the protrusion portion.

4. The penile implant of claim 1, wherein the coupling portion of the first member includes a cavity having a rounded surface.

5. The penile implant of claim 1, wherein the coupling portion of the second member includes a protrusion portion, the protrusion portion having a rounded surface.

6. The penile implant of claim 1, wherein the coupling portion of the first member includes a cavity, the locking portion of the first member being disposed within the cavity.

7. The penile implant of claim 1, wherein the coupling portion of the first member includes a side wall defining a cavity, the locking portion of the first member is a groove defined by the side wall.

8. The penile implant of claim 1, wherein the coupling portion of the second member includes a protrusion portion, the locking portion of the second member being disposed on the protrusion portion.

9. The penile implant of claim 1, wherein the coupling portion of the second member includes a protrusion portion, the locking portion of the second member includes a ridge, the ridge being disposed on the protrusion portion.

10. The penile implant of claim 1, wherein the coupling portion of the second member includes a protrusion portion, the locking portion of the second member includes a projection disposed on the protrusion portion.

11. The penile implant of claim 1, the coupling portion of the second member is a first coupling portion of the second member, wherein the second member includes a second coupling portion, the first coupling portion of the second member including a protrusion portion, the second coupling portion of the second member including a side wall defining a cavity.

12. The penile implant of claim 1, wherein the coupling portion of the first member includes a cavity, the locking portion of the first member includes a projection, the projection being disposed within the cavity.

13. The penile implant of claim 1, wherein the coupling portion of the second member includes a protrusion portion, the locking portion of the second member including a groove defined on the protrusion portion.

14. The penile implant of claim 1, further comprising:
a sheath defining a lumen, the lumen being configured to house the first member and the second member.

15. The penile implant of claim 1, further comprising:
a first end cap coupled to the first member;
a second end cap coupled to the second member; and
a sheath defining a lumen, the lumen being configured to house the first member, the second member, a least a portion of the first end cap, and at least a portion of the second end cap.

16. An apparatus comprising:
an elongate member formed of a plurality of segment member, the elongate member configured to be placed in a first non-linear configuration and in a linear configuration,
a first segment member of the plurality of segment members having a coupling portion and a locking portion,
a second segment member of the plurality of segment members member having a coupling portion and a locking portion, the locking portion of the second segment member including a first flexible tab member and a second flexible tab member.

17. The apparatus of claim 16, wherein the coupling portion of the first segment member is configured to engage the coupling portion of the second segment member to movably couple the first member to the second member.

18. The apparatus of claim 16, wherein the locking portion of the first segment member is configured to engage the locking portion of the second segment member help retain the elongate member in its linear configuration.

19. The apparatus of claim 16, further comprising:
a sheath defining a lumen, the lumen being configured to house the plurality of segment members.

20. A penile implant, comprising:
an elongate member formed of a plurality of segment member, a first end member, and a second end member, the elongate member configured to be placed in a first non-linear configuration and in a linear configuration; and
a sheath defining a lumen, the lumen being configured to house the plurality of segment members, at least a portion of the first end member, and at least a portion of the second end member,
a first segment member of the plurality of segment members having a coupling portion and a locking portion,
a second segment member of the plurality of segment members member having a coupling portion and a locking portion, the locking portion of the second segment including a first flexible tab member and a second flexible tab member.

* * * * *